United States Patent
Tefft et al.

(10) Patent No.: US 7,071,002 B1
(45) Date of Patent: *Jul. 4, 2006

(54) METHOD AND SYSTEM FOR VEHICLE EMISSION TESTING

(75) Inventors: Robert J. Tefft, Crestwood, KY (US); S. Jay Gordon, Louisville, KY (US); Clifton Mahaffey, Louisville, KY (US); Thomas C. Austin, El Dorado Hills, CA (US); Thomas R. Carlson, Roseville, CA (US)

(73) Assignee: Gordon-Darby Systems, Inc., Louisville, KY (US)

( * ) Notice: Subject to any disclaimer, the term of this patent is extended or adjusted under 35 U.S.C. 154(b) by 319 days.

This patent is subject to a terminal disclaimer.

(21) Appl. No.: 10/656,515

(22) Filed: Sep. 5, 2003

Related U.S. Application Data

(63) Continuation-in-part of application No. 09/851,192, filed on May 8, 2001, now Pat. No. 6,623,975.

(60) Provisional application No. 60/202,968, filed on May 9, 2000.

(51) Int. Cl.
- *G01N 33/22* (2006.01)
- *G01N 33/00* (2006.01)
- *G01N 7/00* (2006.01)
- *G01N 33/497* (2006.01)
- *B32B 5/02* (2006.01)

(52) U.S. Cl. ............ 436/137; 422/83; 73/23.31; 73/1.16; 436/143

(58) Field of Classification Search ........... 73/23.31, 73/1.16; 436/137, 143; 422/83
See application file for complete search history.

(56) References Cited

U.S. PATENT DOCUMENTS

| | | | | |
|---|---|---|---|---|
| 4,348,732 A * | 9/1982 | Kreft | ............ | 702/27 |
| 4,586,367 A * | 5/1986 | Lewis | ............ | 73/23.33 |
| 4,727,746 A * | 3/1988 | Mikasa et al. | ............ | 73/23.31 |
| 5,129,257 A * | 7/1992 | Carduner et al. | ............ | 73/116 |
| 5,419,178 A * | 5/1995 | Decker et al. | ............ | 73/23.31 |
| 5,469,731 A * | 11/1995 | Decker et al. | ............ | 73/23.31 |
| 5,639,957 A * | 6/1997 | Zarchy | ............ | 73/23.31 |
| 5,846,831 A * | 12/1998 | Silvis | ............ | 436/55 |
| 5,877,862 A * | 3/1999 | Nelson et al. | ............ | 356/436 |
| 6,016,711 A * | 1/2000 | Ullman et al. | ............ | 73/863.03 |
| 6,308,130 B1 * | 10/2001 | Vojtisek-Lom | ............ | 701/114 |
| 6,623,975 B1 * | 9/2003 | Tefft et al. | ............ | 436/137 |

OTHER PUBLICATIONS

Thomas C. Austin et al., Alternative and Future Technologies for Reducing Greenouse Gas Emissions from Road Vehicles prepared for the Transportation Table Subgroup on Road.

(Continued)

*Primary Examiner*—Jill Warden
*Assistant Examiner*—Brian Sines
(74) *Attorney, Agent, or Firm*—Stites & Harbison, PLLC; David W. Nagle, Jr.

(57) ABSTRACT

A method and system for vehicle emission testing measures pollutant concentration, but then provides for conversion of the measured pollutant concentration into its corresponding pollutant mass, thereby allowing for the calculation of a vehicle's emission test scores for one or more common pollutants in units of mass per distance. Through the use of the method and system of the present invention, significantly more accurate results can be obtained as compared to prior art test methods, and without the implementation, operating, and maintenance costs of comparable test methods.

18 Claims, 4 Drawing Sheets

OTHER PUBLICATIONS

Vehicle Technology and Fuels, Jul. 8, 1999, Report No. SR99-07-01, Sierra Research, Inc., Sacramento, California under subcontract to SENES Consultants Limited.

* cited by examiner

AMBIENT AIR
CONDENSED AIR
CALIBRATION GASES

METHOD AND SYSTEM FOR VEHICLE EMISSION TESTING

CROSS-REFERENCE TO RELATED APPLICATIONS

The present application is a continuation-in-part of U.S. Utility application Ser. No. 09/851,192 filed May 8, 2001, an application claiming priority to U.S. Provisional Patent Application Ser. No. 60/202,958 filed May 9, 2000 now U.S. Pat. No. 6,623,975. Each of the above-referenced applications is incorporated herein by reference.

BACKGROUND OF THE INVENTION

The present application relates to a method and system for vehicle emission testing. Vehicle emissions have long been identified as a major contributor to air pollution. As such, in geographical areas having particularly poor air quality, the United States federal government, through the Environmental Protection agency ("EPA"), has mandated vehicle emission inspection and maintenance programs. The intent or objective of these vehicle emission inspection and maintenance programs is to identify vehicles which are no longer performing acceptably, i.e., vehicles which are releasing polluting emissions in excess of the standards that they were originally certified to meet. Vehicles identified as not performing acceptably, i.e., having excessive emissions, must then be appropriately repaired.

In implementing vehicle emission inspection and maintenance programs, various apparatus, methods, and testing protocols have been developed and are being used across the United States. In this regard, the local municipality or similar governing body normally makes the decision as to which apparatus, method, and/or protocol to employ. For example, some municipalities have opted for centralized testing locations designed for high throughput, others have opted for decentralized testing locations (e.g., at existing garages or repair facilities), and still others have opted for a hybrid centralized/decentralized systems. Furthermore, in some cases, remote sensing devices may be employed to measure the concentration of pollutants emitted by vehicles as they are operated on public roadways. In this regard, such remote sensing devices commonly use infrared or ultraviolet light to measure pollutant concentrations without interfering with or altering vehicle progress. Finally, it is also contemplated that on-board analyzers plumbed directly into a vehicle exhaust system could be used to measure the emissions of vehicles driven on public roadways. In most cases, the ultimate decision as to which apparatus, method, and/or protocol to employ depends on a combination of factors, including, for example: practicality, costs, and input from interested third parties. Thus, there are often wide variations between the apparatus, methods, and/or protocols employed in different geographic areas. Such variations often result in differences in the reliability and accuracy of the testing, along with differences in the amount of labor and skill required to conduct the testing and to maintain the equipment associated with that testing.

A few of the simpler vehicle emission test methods are: (1) the Idle Mode Test, which measures emissions from an idling vehicle; and (2) the Loaded Mode Test, which measures emissions from vehicles driven at a constant speed under a relatively light load. Although these two tests provide general baseline information regarding vehicle emissions, they are not representative of "real world" driving. As a result, both the Idle Mode Test and the Loaded Mode Test often tend to produce false positives. In other words, a vehicle might pass the Idle Mode Test or Loaded Mode Test even though that vehicle is not in compliance with federal guidelines. Quite clearly, such testing failures are potentially detrimental to the air quality of a geographic area because vehicles which require repair are not appropriately identified, thus allowing for excessive release of polluting emissions.

To address these problems, more rigorous test methods and protocols have been developed, including the Acceleration Simulation Mode (ASM) concentration test and Transient Mass Emission Inspections (TMEI). Such test methods are clearly preferred as compared to the Idle Mode Test and the Loaded Mode Test; however, along with improved performance comes increased costs.

First, the ASM concentration test can be used in both centralized and decentralized testing programs. In an ASM concentration test, vehicles are driven at a fixed speed under a relatively heavy load. Nevertheless, because the vehicles are artificially loaded and are not tested across a range of velocities, accelerations, and decelerations representative of "real world" driving conditions used to test and initially certify vehicles for sale, false failures can result. In other words, a vehicle might fail the ASM concentration test even though that vehicle is in compliance with federal standards that the vehicle was initially certified to meet. Although false failures are not detrimental to the air quality of a geographic area, a false failure can be costly to the vehicle owner who must have the vehicle examined at a repair or maintenance facility, and then must have the vehicle re-tested. A high percentage of false failures tends to result in public distrust of vehicle emission testing. Furthermore, false positives are also possible in an ASM concentration test.

Among the most advanced and accurate test methods are Transient Mass Emission Inspections (TMEI), such as the IM240 and IM147. In TMEI, a vehicle is tested at a variety of velocities, accelerations, and decelerations. These velocities, accelerations, and decelerations (collectively referred to as a "drive trace") are representative of "real world" driving conditions and engine loads. Indeed, a common drive trace in TMEI is a subset of the 1372-second drive trace used to initially certify vehicles for sale. For example, an IM240 test includes a series of accelerations, decelerations and speeds ranging from zero miles per hour (MPH) to fifty-six MPH over a 240-second testing period. For the duration of the testing period, emissions, including hydrocarbons (HC), carbon monoxide (CO), carbon dioxide ($CO_2$), and the oxides of nitrogen ($NO_x$), are measured and accumulated over the drive trace and normalized for the distance traveled. This recorded mass per distance, normally reported as grams per mile (GPM), is then reported as the vehicle's test score. The vehicle's test score for each accumulated pollutant is compared to a defined standard for that vehicle and that particular pollutant. A score exceeding the defined standard is considered a failure.

Thus, since pollutant mass is measured in TMEI, as opposed to pollutant concentration (Idle Mode, Loaded Mode and ASM testing), a more accurate determination of the vehicle emission characteristics can be generated. Nevertheless, TMEI have some shortcomings. Conventional TMEI do not lend themselves well to decentralized testing. Furthermore, they are inherently complex and costly to implement, operate, and maintain.

Commonly assigned and co-pending U.S. application Ser. No. 09/851,192, which has been incorporated herein by reference, describes and claims a method and system for vehicle emission testing that relies on transient test drive traces with "real world" velocities, accelerations, decelerations and loading, a method and system that converts measured pollutant concentration into its corresponding pollutant mass at relatively low implementation, operating, and maintenance costs. Specifically, like TMEI testing, the described method and system allows for the calculation of a vehicle's emission test scores for one or more common pollutants in units of mass per distance for subsequent comparison of each such test score to a standard to determine if the vehicle has passed or failed the emissions test. However, in implementing the method and system, characteristic exhaust flow factors that are specific to selected attributes of the vehicle being tested (including, but not limited to make, model, and/or year) are used to allow for a measurement of pollutant concentration to be computationally converted to a measurement of pollutant mass.

The preferred equipment involved in testing in accordance with the teachings of U.S. application Ser. No. 09/851,192 includes: (1) a dynamometer that generates a drive trace that replicates "real world" velocities, accelerations, decelerations, and loading; (2) a narrow sample probe with an associated sampling line; and (3) a series of analyzers for detection of various pollutants or other emissions. Importantly, unlike common TMEI testing, the sample probe is a narrow instrument that is inserted deep into the tailpipe of the vehicle and thus draws samples that are not diluted by ambient air. The actual measured values with respect to particular pollutants are therefore measurements of undiluted or "raw" pollutant concentration.

Through appropriate computational analysis, such measurement of pollutant concentration can be converted to a measurement of pollutant mass. First, calculation of the requisite characteristic exhaust flow factors requires reliance on a reference data set. Accordingly, per-second drive trace test data is extracted from the reference data set, and this data is then characterized or keyed to specific pre-selected vehicle attributes, such as: make, model, model year, manufacturer, inertia weight, and engine displacement. In other words, test records are categorized and placed into reference data subsets based on certain vehicle attributes.

Next, dilution factors and diluted pollutant concentrations can be determined for each data point (i.e., per second of the drive trace) in a particular reference data subset. Each record in the reference data subset includes: the calculated pollutant masses; the background concentrations, i.e., the concentration of each particular pollutant or other emission in ambient air; and the constant volume sampling ("CVS") flow, the rate at which the homogenized mixture of emissions and ambient air traverses the system. From this data, diluted pollutant concentrations and dilution factors can be calculated.

If CVS flow is included in the reference data set, it is then possible to calculate a raw exhaust flow for each pollutant at each data point by dividing the know CVS flow volume by the calculated dilution factor. If the CVS flow is not included in the reference data set, a slightly more complicated calculation, as described below, is required to obtain the raw exhaust flow.

In practice, the actual raw exhaust flow will vary somewhat between even essentially identical vehicles, i.e. those vehicles defined by the same pre-selected attributes. Therefore, an optimum exhaust flow or "Exhaust Flow Factor," an exhaust flow that best characterizes the vehicles defined by specific attributes, is calculated for each second of the drive trace. In this regard, as the computational steps set forth in U.S. application Ser. No. 09/851,192 demonstrate, the Exhaust Flow Factor, the exhaust flow that best characterizes a vehicle defined by specific attributes, is a function of the raw concentration and actual mass of each pollutant at each second of the drive trace.

Once the Exhaust Flow Factor has been determined for vehicles defined by the same pre-selected attributes for each second of the drive trace, the concentration of a specific pollutant at any second of the drive trace can be reported in terms of mass. Specifically, the measured pollutant concentration data is obtained through testing. This concentration data is converted to mass data by multiplying each concentration measurement by the Exhaust Flow Factor (which is derived from the reference data set) at each second of the drive trace, creating an emissions profile for each measured pollutant. The total mass then can be determined by integrating the emission profile over the duration of the test.

Although the method and system described in U.S. application Ser. No. 09/851,192 adequately addresses many of the problems and issues associated with prior art test methods and protocols, since it relies on a reference data set, it may not be well-suited for all circumstances. For example, in testing newer model vehicles, sufficient data may not be available to derive an appropriate Exhaust Flow Factor.

It is therefore a paramount object of the present invention to provide an alternate method and system for vehicle emission testing that converts measured pollutant concentration into its corresponding pollutant mass at relatively low implementation, operating, and maintenance costs.

This and other objects and advantages of the present invention will become apparent upon a reading of the following description.

SUMMARY OF THE INVENTION

The present invention is a method and system for vehicle emission testing that converts measured pollutant concentration into its corresponding pollutant mass at relatively low implementation, operating, and maintenance costs, and thus allows for the calculation of a vehicle's emission test scores for one or more common pollutants in units of mass per distance.

In general, the conversion of measured pollutant concentration into its corresponding pollutant mass in accordance with the method and system of the present invention is a six-step process: (1) measuring vehicle velocity, acceleration rate, and raw pollutant concentrations; (2) calculating Total Drive Wheel Power Demand during each second of the test; (3) determining engine load and speed as a function of Total Drive Wheel Power Demand; (4) determining instantaneous fuel consumption; (5) calculating exhaust flow rate as a function of instantaneous fuel consumption; and (6) converting measured pollutant concentration into its corresponding pollutant mass.

Through the use of the method and system of the present invention, significantly more accurate results can be obtained as compared to prior art test methods, and without the implementation, operating, and maintenance costs of comparable test methods.

DETAILED DESCRIPTION OF THE PRESENT INVENTION

Figure 1:
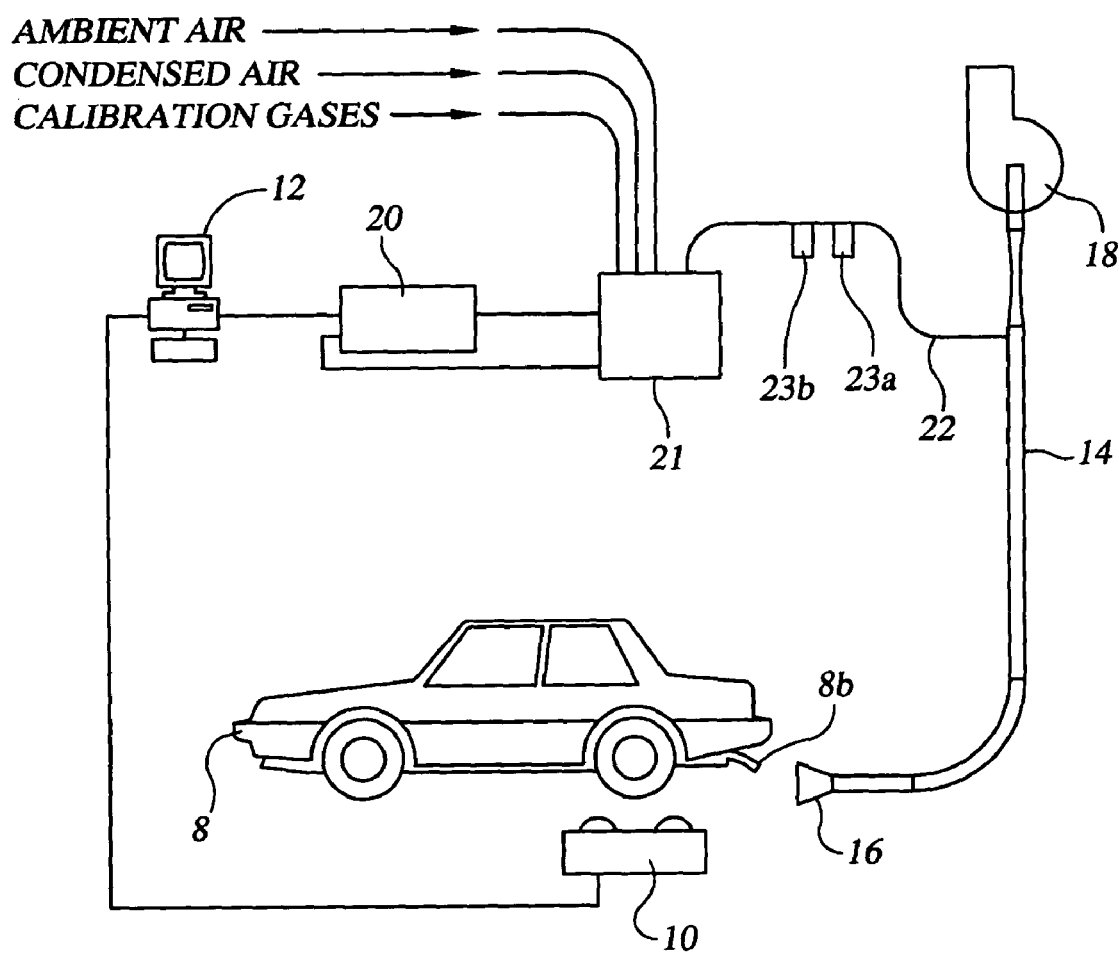
FIG. 1 is a schematic view of the equipment involved in typical prior art Transient Mass Emission Inspections ("TMEI")

The present invention is a method and system for vehicle emission testing that converts measured pollutant concentration into its corresponding pollutant mass at relatively low implementation, operating, and maintenance costs. Specifically, the method and system of the present invention allows for the calculation of a vehicle's emissions (and resultant test scores) for one or more common pollutants in units of mass per distance, thus allowing for subsequent comparison of each such test score to a standard to determine if the vehicle has passed or failed the emissions test. Through the use of the method and system of the present invention, significantly more accurate results can be obtained as compared to Idle Mode, Loaded Mode, ASM, remote sensing and similar testing methods, but without the implementation, operating, and maintenance costs of TMEI.

As described above with reference to commonly assigned and co-pending U.S. application Ser. No. 09/851,192, it is possible to calculate a vehicle's emissions (and resultant test scores) for one or more common pollutants through reliance on a reference data set. Specifically, in such a method and system, characteristic exhaust flow factors that are specific to selected attributes of the vehicle being tested (including, but not limited to make, model, and/or year) are used to convert a measurement of pollutant concentration to a measurement of pollutant mass. Rather than rely on such a reference data set, the method and system of the present invention depends on a determination of the approximate exhaust flow rate of a test vehicle based on the manner in which that vehicle is loaded and certain key vehicle characteristics that govern the amount of fuel consumed during an emissions test. For the vast majority of gasoline-powered vehicle produced since 1981, the exhaust flow rate can be accurately calculated from the fuel consumption of the vehicle assuming stoichiometric conditions, and then using this exhaust flow rate, measured pollutant concentration can be converted into its corresponding pollutant mass. For greater accuracy, the instantaneous air-fuel ratio can also be calculated from the ratio of carbon dioxide and carbon monoxide in the exhaust and the absolute concentration of carbon dioxide.

Before describing the computational details of the method and system of the present invention, it is useful to review the method and system described and claimed in commonly assigned and co-pending U.S. application Ser. No. 09/851, 192, since its objectives and implementation are similar in many aspects to the present invention. In the preferred implementation described in U.S. application Ser. No. 09/851,192, the use of a reference data set is key. The requisite reference data set was compiled through the TMEI program in Maricopa County, Arizona. Specifically, the reference data set is comprised of a random, representative sample of the actual emissions testing records from the TMEI program in Maricopa County, Arizona. Each record in the reference data set identifies the tested vehicle by make, model, model year, manufacturer, inertia weight, and engine displacement. Each record further provides the constant volume sampling (CVS) flow and drive trace associated with the test, as will be further described below, along with the actual results of the test—the measured pollutant masses for the tested vehicle for each second of the drive trace.

This particular reference data set was selected because the Maricopa County TMEI program is widely recognized within the industry for the accuracy and consistency of its testing, and thus often serves as a standard against which other vehicle emissions tests are compared. Nevertheless, the use of this particular data set is not intended to be limiting, but for illustrative purposes only. Other reference data sets may be also be used in accordance with the present invention without departing from the spirit and scope of the present invention.

Figure 1A:
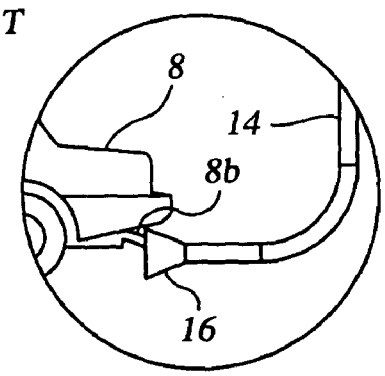
FIG. 1a is an enlarged view of the fitting of an emissions collection vent with a conical inlet port over the tailpipe of the vehicle to be tested in typical prior art Transient Mass Emission Inspections ("TMEI")

As mentioned above, the Maricopa County TMEI program is widely recognized within the industry for the accuracy and consistency of its testing. Referring now to FIGS. 1 and 1a, the equipment involved in testing in the Maricopa County TMEI program includes: (1) a dynamometer and associated controller 10 operably connected to a computer 12 or similar microprocessor which is programmed to generate a drive trace that replicates "real world" velocities, accelerations, decelerations, and loading; (2) a constant volume sampling (CVS) system generally comprised of an emissions collection vent 14 with a conical inlet port 16 and a high-pressure blower 18; and (3) a series of analyzers 20 for detection of various pollutants or other emissions, e.g., HC, CO, $CO_2$, and $NO_x$, said analyzers 20 being in gaseous communication with a sample and calibration gas control system 21, which in turn is operably connected to the CVS system by one or more sampling lines 22. Of final note, the system may also include one or more sample filters 23a, 23b. The primary filter 23a removes extraneous materials, such as rust pieces, that are drawn into the collection vent 14. The secondary filter 23b removes smaller extraneous materials that were able to pass through the primary filter 23a. In general, such filters are employed to extend the life of the testing equipment and to ensure the accuracy of the testing process.

In this prior art test method and system, since the conical inlet port 16 of the collection vent 14 fits around the tailpipe 8b of the vehicle 8 being tested, the extracted tailpipe emissions sample includes essentially all of the vehicle's tailpipe emissions. The blower 18 also introduces some ambient air into the sample, turbulently homogenizing the mixture of raw emissions and ambient air so that the ambient air dilutes the tailpipe emissions. A small portion of this homogenized mixture of raw emissions and ambient air is then siphoned off through one or more sampling lines 22 and introduced into the series of analyzers 20 for detection of various pollutants or other emissions, e.g., HC, CO, $CO_2$, and $NO_x$, each analyzer essentially generating an emission profile for a specific type of pollutant.

The analyzers 20 are calibrated to detect pollutant concentration in terms of:

$$\frac{\text{Parts Pollutant}}{z \text{ Parts}} \text{ where } z = \quad (1)$$

-continued 1,000,00 or 100 (depending on the pollutant)

However, since the raw emissions are mixed and homogenized with ambient air to generate a constant volume referred to as a "sample volume," and the densities (mass per sample volume) of the pollutants are known values, the output from the analyzers can be calculated in terms of mass for each second of the drive trace, specifically:

$$\text{Mass}_{Pollutant} = \frac{\text{Parts Pollutant}}{z \text{ Parts}} \times \frac{\text{Mass}}{\text{Sample Volume}} \times \text{Sample Volume} \quad (2)$$

If necessary, this calculation can be further refined to take into account environmental factors, such as the humidity.

By plotting the calculated mass at each second of the drive trace, an emissions profile for each measured pollutant emerges. The total mass then can be determined by integrating the emission profile over the duration of the test.

Finally, from the drive trace, the number of miles "driven" over the duration of the test is determined. For any particular pollutant, the specific vehicle's test "score" is calculated by dividing the total mass of the specific pollutant by the number of miles "driven." Of course, the calculated test score for the particular pollutant is compared to the defined standard for that vehicle and that pollutant. A score exceeding the defined standard is considered a failure.

Figure 2:
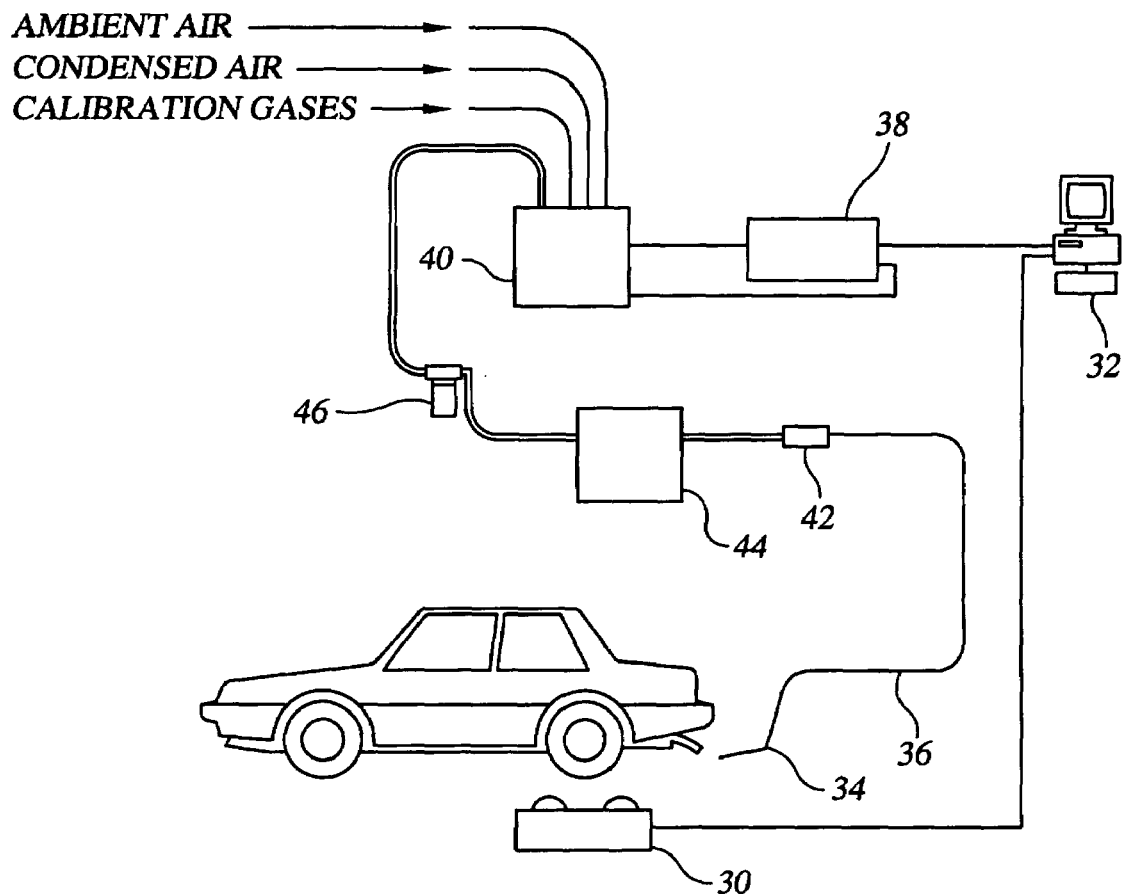
FIG. 2 is a schematic view of the equipment involved in the method and system of the present invention.
Figure 2A:
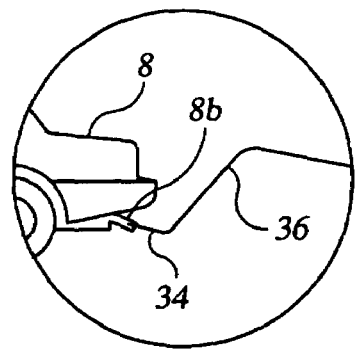
FIG. 2a is an enlarged view of the insertion of a sampling probe into the tailpipe of the vehicle to be tested in the method and system of the present invention.

The method and system described and claimed in U.S. application Ser. No. 09/851,192 also allows for measurement of pollutant mass instead of pollutant concentration, but does not require the elaborate CVS system and associated equipment described above and as used in Maricopa County TMEI program. Specifically, referring to FIGS. 2 and 2a, the preferred equipment involved in testing in accordance with the teachings of U.S. application Ser. No. 09/851,192 includes: (1) a dynamometer and associated controller 30 operably connected to a computer 32 or similar microprocessor which is programmed to generate a drive trace that replicates "real world" velocities, accelerations, decelerations, and loading; (2) a narrow sample probe 34 with an associated sampling line 36; and (3) a series of analyzers 38 for detection of various pollutants or other emissions, e.g., HC, CO, $CO_2$, and $NO_x$, said analyzers 38 being in gaseous communication with a sample and calibration gas control system 40, which in turn is operably connected to the sampling line 36.

Of further note, this system preferably includes a primary filter 42 for removing extraneous materials, such as rust pieces, that are drawn into the sampling line 36. Subsequent to passing through the primary filter 42, collected samples are passed through a refrigerant dryer 44 which removes moisture from the collected sample without adversely affecting pollutant measurements. It is important to remove moisture in this manner to prevent condensation as condensation in the sampling system can affect pollutant measurement and also lead to system failure. Then, the collected sample is passed through a secondary filter 46 which removes smaller extraneous materials that were able to pass through the primary filter 42.

In this regard, the testing equipment is very similar to that commonly used in current Idle Mode, Loaded Mode and ASM test methods. Unlike TMEI testing, the sample probe 34 is a narrow instrument that is inserted deep into the tailpipe 8b of the vehicle 8, rather than fitting over and around the tailpipe, and thus draws samples that are not diluted by ambient air. The actual measured values with respect to particular pollutants are therefore measurements of pollutant concentration. Nevertheless, through appropriate computational analysis, the measurement of pollutant concentration can be converted to a measurement of pollutant mass, as is described in detail below.

Figure 3:
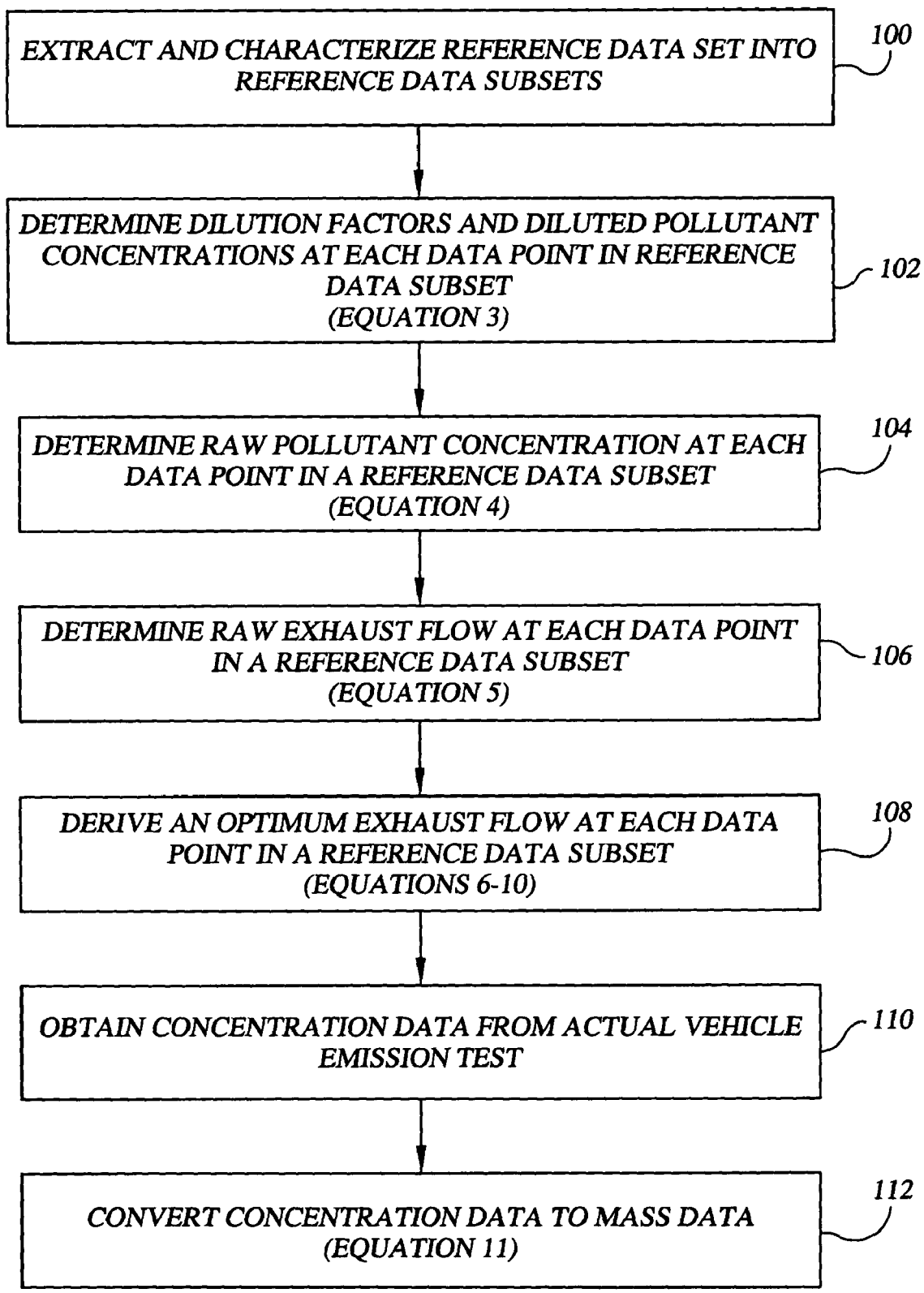
FIG. 3 is a flow chart depicting the steps involved in vehicle emission testing in accordance with the teachings of commonly assigned and co-pending U.S. application Ser. No. 09/851,192.

Referring now to FIG. 3, the method and system described and claimed in U.S. application Ser. No. 09/851,192 is summarized in flow chart form. First, as mentioned above, calculation of the requisite characteristic exhaust flow factors requires reliance on a reference data set, such as the above-mentioned reference data set from the TMEI program in Maricopa County, Arizona—a data set compiled through IM240 testing. Accordingly, the first step in the flow chart of FIG. 3 is the extraction and characterization of the reference data set, as indicated at block 100. In this regard, per-second drive trace test data is extracted, and this data is characterized or keyed to specific pre-selected vehicle attributes, such as: make, model, model year, manufacturer, inertia weight, and engine displacement. In other words, test records are categorized and placed into reference data subsets based on certain vehicle attributes. For example, a reference data subset may include test records for all 1998 Honda Accords having a four-cylinder engine. Of course, data could be extracted in characterized in a number of ways based on various combinations of vehicle attributes as desired by the user.

Next, dilution factors and diluted pollutant concentrations can be determined for each data point (i.e., per second of the drive trace) in a particular reference data subset, as indicated at block 102 of FIG. 3. Specifically, each record in the reference data subset includes: the actual measured pollutant masses; the background concentrations, i.e., the concentration of each particular pollutant or other emission in ambient air; and the CVS flow, the rate at which the homogenized mixture of emissions and ambient air traverses the system as measured in cubic feet per second. With such data, dilution factors and diluted pollutant concentrations can be calculated by simultaneously solving the following equation for all pollutants for each data point.

$$\text{Actual Mass}_X = (\text{CVS Flow} * \text{DensF}_X) * \{DC_X - [BC_X * (1 - 1/\text{DilF})]\} \quad (3)$$

where

Actual Mass$_X$=the mass of HC, CO, $CO_2$, and $NO_s$ (as reported in the reference data set)

DensF$_X$=Gas-specific density factor (per 40 C.F.R. 81–99, Section 86,144–78)

DC$_X$=Diluted Concentration

BC$_X$=Background Concentration (as reported in the reference data set)

DilF=Dilution Factor

=13.4/(Diluted $CO_2$+Diluted CO+Diluted HC) (per IM240 and Evap Technical Guidance EPA-AA-RSPD-IM-98-1)

If the CVS Flow was stored in the reference data set, raw exhaust volume can be calculated by dividing the CVS Flow by the dilution factor. If the CVS Flow was not stored in the reference data set, then, multiplying the dilution factors by the respective diluted pollutant concentrations generates a raw pollutant concentration for each data point in the reference data subset, as indicated at block 104 of FIG. 3:

$$\text{Raw Concentration}_X = \text{DilF} * \text{Diluted Concentration}_X \quad (4)$$

With this information, and the pollutant mass data provided through the reference data subset, it is then possible to calculate a raw exhaust flow for each pollutant at each data point, as indicated at block 106 of FIG. 3, as follows:

$$\text{Raw Exhaust Flow} = \text{Actual Mass}_X/(\text{Raw Concentration}_X * \text{DensF}_X) \quad (5)$$

In practice, the actual raw exhaust flow will vary somewhat between even essentially identical vehicles, i.e. those vehicles defined by the same pre-selected attributes. Therefore, an optimum exhaust flow or "Exhaust Flow Factor," an exhaust flow that best characterizes the vehicles defined by specific attributes, must be calculated for each second of the drive trace, as indicated at block 108 of FIG. 3. Specifically, the optimum exhaust flow will be the value at which error is minimized at any particular second. In this regard, the "Predicted Mass$_X$," the mass$_X$ for a specified pollutant, is a product of the known raw concentration and the unknown Exhaust Flow Factor:

$$\text{Predicted Mass}_X = \text{Raw Concentration}_X * \text{Exhaust Flow Factor} \quad (6)$$

Since the Actual Mass$_X$ of each particular pollutant is known from the reference data, the error at any second for any particular pollutant can be determined as follows:

$$\text{Error}_X = [(\text{Predicted Mass}_X/\text{Actual Mass}_X) - 1]^2 \quad (7)$$

Substituting for Predicted Mass$_X$:

$$\text{Error}_X = \{[(\text{Raw Concentration}_X * \text{Exhaust Flow Factor})/\text{Actual Mass}_X] - 1\}^2 \quad (8)$$

Summing the error over all the pollutants and all members of the data subset produces a single error value:

$$\text{Error}_N = \sum_x \sum_{n=1}^{N} \text{Error}_{X_n} \quad (9)$$

where x=HC, CO, or NO$_x$
n=individual test record
N=total number of test records in data set Substituting for Error$_X$ for each pollutant and differentiating with respect to the Exhaust Flow leads to Error$_N$ being at a minimum when:

$$\text{Exhaust Flow Factor} = \frac{\sum_x \sum_{n=1}^{N} (\text{Raw Concentration}_{X_n}/\text{Actual Mass}_{X_n})}{\sum_x \sum_{n=1}^{N} (\text{Raw Concentration}_{X_n}/\text{Actual Mass}_{X_n})^2} \quad (10)$$

where x=HC, CO, or NO$_x$
n=individual test record
N=total number of test records in data set In short, through the derivation set forth in equations (6)–(10), it becomes clear that the Exhaust Flow Factor, the exhaust flow that best characterizes a vehicle defined by specific attributes, is a function of the raw concentration and actual mass of each pollutant at each second of the drive trace.

Once the Exhaust Flow Factor has been determined for vehicles defined by the same pre-selected attributes for each second of the drive trace, the concentration of a specific pollutant at any second of the drive trace can be reported in terms of mass. Specifically, as indicated at block 110 of FIG. 3, the measured pollutant concentration data is obtained through testing as described above with reference to FIGS. 2 and 2A. As indicated at block 112 of FIG. 3, the concentration data is converted to mass data as follows:

$$\text{Mass}_{Pollutant} = \frac{\text{Parts Pollutant}}{z \text{ Parts}} \times \frac{\text{Mass}}{\text{Volume}} \times \text{Exhaust Flow Factor} \quad (11)$$

where (Parts Pollutant/z Parts)=concentration as measured by the pollutant analyzer (Mass/Volume)=pollutant density (a known value)

Then, as with TMEI, by plotting the calculated mass at each second of the drive trace, an emissions profile for each measured pollutant emerges. The total mass then can be determined by integrating the emission profile over the duration of the test.

Finally, the number of miles "driven" over the duration of the test is determined. For any particular pollutant, the specific vehicle's test "score" is calculated by dividing the total mass of the specific pollutant by the number of miles "driven." Of course, the calculated test score for the particular pollutant is compared to the defined standard for that vehicle and that pollutant. A score exceeding the defined standard is considered a failure.

The method and system of the present invention is similar to that described above and in U.S. application Ser. No. 09/851,192. However, derivation of the Exhaust Flow Factor does not rely on a reference data set, but rather such an Exhaust Flow Factor (i.e., the exhaust flow rate) is calculated based on a determination of the fuel consumption of the vehicle and the known relationship between fuel consumption and exhaust volume under either stoichiometric or non-stoichiometric conditions.

Figure 4:
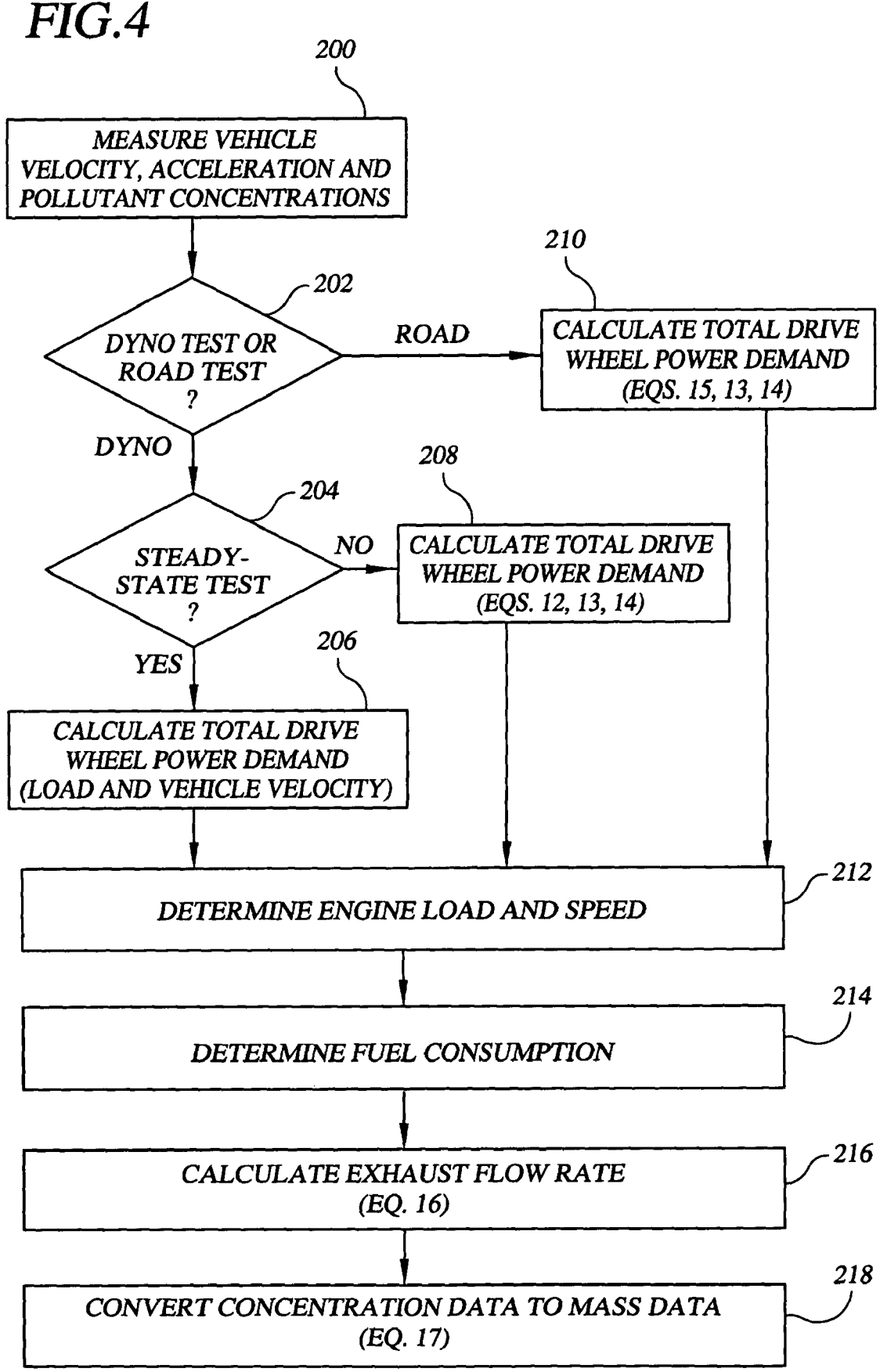
FIG. 4 is a flow chart depicting the steps involved in vehicle emission testing in accordance with the method and system of the present invention.

Referring now to FIG. 4, the method and system of the present invention is summarized in flow chart form. At the outset, it should be noted that the computational analysis is partially dependent on the type of test being performed. Specifically, as shown in the flow chart of FIG. 4, the computational analysis varies depending on whether the test is performed on a dynamometer or on the road, and in the case of dynamometer testing, whether the test is performed under steady-state or transient conditions. In any event, regardless of the type of testing, the conversion of measured pollutant concentration into its corresponding pollutant mass in accordance with the method and system of the present invention is generally a six-step process: (1) measuring vehicle velocity, acceleration rate, and raw pollutant concentrations; (2) calculating Total Drive Wheel Power Demand during each second of the test; (3) determining engine load and speed as a function of Total Drive Wheel Power Demand; (4) determining instantaneous fuel consumption; (5) calculating exhaust flow rate as a function of instantaneous fuel consumption; and (6) converting measured pollutant concentration into its corresponding pollutant mass. Each of these steps is described in detail below.

Referring still to the flow chart of FIG. 4, the first step is the measurement of vehicle velocity, acceleration rate, and raw pollutant concentrations, as indicated at block 200. In the case of dynamometer testing, the measurement of raw pollutant concentrations, along with measurements of vehicle velocity and acceleration rate, is accomplished as described above with reference to FIGS. 2 and 2A.

However, as mentioned above, it is also contemplated that the method and system of the present invention could be implemented as part of a road testing program (through remote sensing devices or on-board analyzers) without departing from the spirit and scope of the present invention. In such circumstances, an accurate speed-time trace for the vehicle being tested must be obtained through the use of appropriate devices installed on the vehicle. For example, it is contemplated that the appropriate speed and time measurements could be taken from: the original equipment speed sensor (which commonly measures the rotational speed of the transmission output shaft); a supplemental speed-measuring device, such as a driveshaft-mounted speed sensor; or a global positioning device. Alternatively, when emissions are being measured by remote sensing devices, speed and time measurements could also be taken remotely, for example, by recording the elapsed time periods in which the front wheels of the vehicle make contact with pressure sensing lines that have been laid across the roadway at predetermined intervals. As yet a further alternative, in order to obtain more detailed information regarding the speed-time profile of the vehicle, a laser-based rangefinder system could also be employed.

Regardless of the specific measurement technique used, the first step in the preferred method of the present invention again is the measurement of vehicle velocity, acceleration rate, and raw pollutant concentrations, as indicated at block 200 of FIG. 4.

The second step in the preferred method of the present invention involves the calculation of Total Drive Wheel Power Demand during each second of the test. Since this portion of the computational analysis varies depending on whether the test is performed on a dynamometer or on the road, and in the case of dynamometer testing, whether the test is performed under steady-state or transient conditions, referring still to the flow chart of FIG. 4, a determination is made as to whether the test was a dynamometer test or a road test, as indicated at decision 202.

In the case of a dynamometer test, a determination must then be made as to whether the test was conducted under steady-state or transient conditions, as indicated at decision 204. If the test was conducted under steady-state conditions, similar to the above-described ASM test, the Total Drive Wheel Power Demand is simply the constant load applied by the dynamometer during the test multiplied by the velocity of the vehicle at each second of the test, as indicated at block 206 of FIG. 4. On most dynamometers, the total power to be absorbed at a particular velocity can be set by the operator, and the dynamometer will adjust the load accordingly to achieve the desired power level.

If the test was conducted under transient conditions, i.e., at a variety of velocities, accelerations, and decelerations representative of "real world" driving conditions and engine loads, the Total Drive Wheel Power Demand is a sum of the Road Load Power and the Acceleration Power. The "Road Load Power" is the power applied by the dynamometer to simulate the combination of rolling resistance and aerodynamic drag, whereas the "Acceleration Power" is the power applied by the dynamometer to simulate the resistance caused by the mass of the vehicle during changes in velocity. The Road Load Power (kW) applied by most dynamometers increases with velocity in a manner consistent with a quadratic equation of the form:

$$\text{Road Load Power} = a + bV + cV^2 \quad (12)$$

where a, b, and c are constants and V is the velocity of the vehicle.

Since the coefficients a, b, and c will be known for a particular dynamometer, the road load portion of the Total Drive Wheel Power Demand can be readily calculated using equation (12).

To calculate the Acceleration Power (kW), a standard equation is also used:

$$\text{Acceleration Power} = m*a*V*(1 \text{ h}/3600 \text{ s}) \quad (13)$$

where
m=loaded vehicle mass (kg)
a=the instantaneous acceleration (m/s$^2$)
V=the instantaneous vehicle velocity (km/h)

With respect to equation (13), during dynamometer testing, it may not be possible to set the dynamometer to simulate the vehicle mass precisely. Dynamometers without electrical inertia simulation require the operator to select from a limited number of inertia weight categories. When using such dynamometers, the mass term equation (13) should be assigned a value equal to the loaded vehicle mass being simulated by the dynamometer.

The Total Drive Wheel Power Demand can then be calculated by summing the Road Load Power and Acceleration Power, as indicated at block 208 of FIG. 4, as follows:

$$\text{Total Drive Wheel Power Demand} = \text{Road Load Power} + \text{Acceleration Power} \quad (14)$$

Finally, in the case of a road test in which testing is accomplished through remote sensing devices or on-board analyzers, the Road Load Power can be calculated from available information regarding the grade of the roadway, the weight of the vehicle, the rolling resistance of the tires on the roadway surface, the frontal area of the vehicle, and the aerodynamic drag coefficient of the vehicle. Furthermore, additional factors, such as roadway curvature and wind, can also be accounted for, but are generally not computationally significant. Therefore, the Road Load Power (kW) can be calculated as follows:

$$\begin{array}{c}\text{Road Load}\\\text{Power}\end{array} = [(f*m*g) + (0.0386*\rho*C_d*A*V^2) + (0.01*m*g*p)]*\frac{V}{3600 s/h} \quad (15)$$

where
f=the coefficient of rolling resistance (approx. 0.01 for pneumatic tires on concrete)
m=loaded vehicle mass (kg)
g=the universal gravitational constant (9.81 M/s$^2$)
0.0386=constant (equivalent to constant of 0.5 with velocity in m/s)

ρ=the density of air (kg/m³)
$C_d$=the aerodynamic drag coefficient
A=the frontal area of the vehicle (m²)
V=the velocity of the vehicle (km/h)
p=the grade percentage (rise over run*100)
0.01=conversion factor (grade percentage to tangent of road angle)

Equation (15) is commonly incorporated into computer-based vehicle simulation models to calculate engine power requirements and vehicle fuel economy, such as the VEHSIM model developed by Sierra Research, Inc. of Sacramento, Calif.

As in the case of dynamometer testing, the Acceleration Power must also be calculated and added to the Road Load Power to obtain the Total Drive Wheel Power Demand, as described above with respect to equations (13) and (14), and as indicated at block 210 of FIG. 4. These calculations are also commonly incorporated into computer-based vehicle simulation models, such as the VEHSIM model mentioned above.

Once the Total Drive Wheel Power Demand has been calculated, engine load and speed can be determined, as indicated at block 212 of FIG. 4. In this regard, the power that must be supplied by the vehicle engine exceeds the Total Drive Wheel Power Demand because of inefficiencies in the vehicle drive train and parasitic loads on the engine, such as the power required to operate vehicle accessories. In vehicles equipped with automatic transmissions, drive train efficiency varies with vehicle velocity and the Total Drive Wheel Power Demand depending on the extent to which the torque converter is being used to increase the effective gear ratio of the transmission. Specifically, the relationship between engine speed and vehicle velocity is determined by tire size, axle ratio, transmission gear position, and torque converter slip. The combined effect of the drive train on engine speed and power can be determined through the use of a computer software module that characterizes the operation of the drive train over the full range of vehicle operating conditions. Such software must contain "shift logic" that reflects how transmission gears are selected as a function of engine load and speed. As described in a report entitled "Alternative and Future Technologies for Reducing Greenhouse Gas Emissions from Road Vehicles" authored by T. C. Austin et al. of Sierra Research, Inc. of Sacramento, Calif. (Report No. SR99-07-01), commercially available computer models can be used to accurately estimate engine load and speed as a function of drive wheel power and vehicle velocity, including, for example, the VEHSIM model developed by Sierra Research, Inc. This report is incorporated herein by this reference.

The fourth step in the preferred method of the present invention involves the determination of fuel consumption based on the estimated engine load and speed, as indicated at block 214 of FIG. 4. Specifically, the instantaneous fuel consumption rate can be estimated with the use of a representative engine map, which is a tabular or graphical representation of fuel consumption as a function of engine load and speed. The operating conditions covered by the engine map must range from idle speed with no engine load to maximum engine speed at "wide open throttle." An interpolation routine can be used to estimate fuel consumption for load and speed combinations that lie between combinations included in a tabular engine map, and such an interpolation routine is commonly incorporated into computer-based vehicle simulation models.

Although there are significant differences in the fuel economy of the various makes and models of vehicles, there are relatively minor differences in the maximum efficiency of the conventional gasoline engines used in these vehicles. Most of the differences in fuel economy can be explained by differences in vehicle weight and engine size. In this regard, because the efficiency of a conventional gasoline-fueled engines is strongly affected by the percentage of maximum power at which it is running, a larger engine, which generally operates at a lower percentage of maximum power, has a much poorer fuel economy. As demonstrated in the above-referenced report entitled "Alternative and Future Technologies for Reducing Greenhouse Gas Emissions from Road Vehicles" (which has been incorporated herein by reference), a "generic" engine map, which is constructed by blending several representative engine maps together, can be used to accurately estimate the fuel economy of a broad range of vehicles provided the map is "re-sized" to match the displacement of the particular vehicle being evaluated. Again, commercially available computer models can be used to provide and re-size the requisite engine maps, such as the VEHSIM model developed by Sierra Research, Inc.

Once instantaneous fuel consumption has been determined based on the estimated engine load and speed, the exhaust flow rate (or the "Exhaust Flow Factor") can be calculated, as indicated at block 216 of FIG. 4. In this regard, virtually all gasoline-fueled passenger vehicles (i.e., cars and light trucks) being produced for sale in the United States are equipped with exhaust gas oxygen sensors and feedback control systems designed to maintain a stoichiometric air-fuel ratio. The stoichiometric air-fuel ratio is the air-fuel ratio that provides just enough air to completely burn all of the fuel. Therefore, the amount of exhaust gas generated by the combustion of stoichiometric air-fuel ratios can be calculated by assuming the perfect combustion of a hydrocarbon representing commercial gasoline. For example, non-oxygenated gasoline can be reasonably represented by octane: $C_8H_{18}$. The completed combustion of octane in air is represented by the following equation:

$$C_8H_{18}+12.5O_2+47N_2>8CO_2+9H_2O+47N_2 \quad (16)$$

where $C_8H_{18}$ is one octane molecule (with an atomic weight of 114 grams/mole);
  12.5 $O_2$=the amount of oxygen necessary to completely oxidize all of the carbon to carbon dioxide;
  47 $N_2$=the amount of nitrogen associated with each 12.5 molecules of oxygen, assuming a ratio of oxygen to nitrogen of 21/79;
  8 $CO_2$=the amount of carbon dioxide produced by burning one octane molecule; and
  $9H_2O$=the amount of water vapor produced by burning one octane molecule.

As equation (16) indicates, the combustion of 114 grams of octane under stoichiometric conditions produces 64 moles of exhaust gases. At standard conditions, the volume associated with these 64 moles of exhaust (at 22.4 liters per mole) is 1,434 liters or 50.6 cubic feet. Under cold start conditions or wide open throttle, the air-fuel ratio may be somewhat richer than stoichiometric. Furthermore, during deceleration, many vehicles incorporate a fuel shut-off that causes the air-fuel ratio to become extremely lean. Nevertheless, cold start, wide open throttle, and declaration are not operating conditions that correlate well with average vehicle emissions. Therefore, vehicle emissions tests have been developed for the purpose of characterizing the emissions of vehicles under conditions in which most vehicle are operating, i.e., in conditions in which almost all of the exhaust gases are produced under stoichiometric conditions. Thus, assuming stoichiometric conditions is an acceptable and reasonable basis for calculating the exhaust flow rate. However, as mentioned above, a variation of the method described herein would account for the presence of nonstoichiometric conditions based on the ratio of carbon monoxide to carbon dioxide in the exhaust and from the absolute concentration of carbon dioxide in the raw exhaust.

As with the method and system described and claimed in U.S. application Ser. No. 09/851,192, once the exhaust flow rate (or "Exhaust Flow Factor") has been calculated, the concentration of a specific pollutant at any second of the drive trace can be reported in terms of mass. Specifically, as indicated at block 218 of FIG. 4, the measured pollutant concentration data, which may be obtained through testing as described above with reference to block 200 of FIG. 4, is converted to mass data as follows:

$$\text{Mass}_{Pollutant} = \frac{\text{Parts Pollutant}}{z \text{ Parts}} \times \frac{\text{Mass}}{\text{Volume}} \times \text{Exhaust Flow Factor} \quad (17)$$

where (Parts Pollutant/z Parts)=concentration as measured by the pollutant analyzer (Mass/Volume)=pollutant density (a known value)

Then, by plotting the calculated mass at each second of the drive trace, an emissions profile for each measured pollutant emerges. The total mass then can be determined by integrating the emission profile over the duration of the test.

Finally, as with the method and system described and claimed in U.S. application Ser. No. 09/851,192, the number of miles "driven" over the duration of the test is determined. For any particular pollutant, the specific vehicle's test "score" is calculated by dividing the total mass of the specific pollutant by the number of miles "driven." Of course, the calculated test score for the particular pollutant is compared to the defined standard for that vehicle and that pollutant. A score exceeding the defined standard is considered a failure.

It is contemplated and preferred that all required computation is accomplished through a digital computer program. With benefit of the foregoing description, such programming is readily accomplished by one of ordinary skill in the art using known programming languages and techniques.

It will be obvious to those skilled in the art that modifications may be made to the preferred embodiments described herein without departing from the spirit and scope of the present invention.

What is claimed is:

1. A method for determining a mass of a pollutant in an emissions sample obtained from a particular vehicle, comprising the steps of:

extracting the emissions sample from the particular vehicle as it is operated over a testing period comprised of one or more discrete time intervals;

determining instantaneous fuel consumption of the particular vehicle;

calculating an exhaust flow rate based on the instantaneous fuel consumption of the particular vehicle at each discrete time interval;

analyzing the emissions sample extracted from the particular vehicle to measure the concentration of the pollutant in said sample at each discrete time interval; and determining the mass of the pollutant at each discrete time interval by multiplying the exhaust flow rate by the measured concentration of the pollutant by a known density of the pollutant.

2. The method as recited in claim 1, and further comprising the steps of:

plotting the mass of the pollutant over the testing period to generate an emission profile; and integrating the emission profile over the testing period to determine a total mass of the pollutant.

3. The method as recited in claim 2, and further comprising the steps of:

dividing the total mass of the pollutant by the distance traveled over the testing period to calculate a test score for the pollutant; and comparing said test score against a defined standard, wherein a test score exceeding the defined standard is considered a failure.

4. The method as recited in claim 1, in which determining instantaneous fuel consumption of the particular vehicle comprises the following sub-steps:

measuring a velocity and an acceleration rate of the particular vehicle;

calculating a total drive wheel power demand at each discrete time interval of the testing period based on the velocity, the acceleration rate, and certain physical characteristics of the particular vehicle;

determining an engine load and an engine speed as a function of the total drive wheel power demand; and estimating the instantaneous fuel consumption of the particular vehicle using a representative engine map relating fuel consumption to engine load and engine speed.

5. The method as recited in claim 4, in which the calculation of the exhaust flow rate based on the instantaneous fuel consumption of the particular vehicle is premised on an assumed combustion of fuel with a stoichiometric air-fuel ratio.

6. The method as recited in claim 1, in which said representative engine map is a generic engine map constructed by blending several representative engine maps together.

7. The method as recited in claim 1, in which said representative engine map is re-sized to match the displacement of the particular vehicle.

8. The method as recited in claim 6, in which said representative engine map is re-sized to match the displacement of the particular vehicle.

9. The method as recited in claim 1, in which the extraction and analysis of the emissions sample from the particular vehicle is accomplished by:

a narrow sample probe for insertion into the tailpipe of the particular vehicle;

a sampling line operably connected to said sample probe; and an analyzer for detection of the pollutant associated with and in gaseous communication with a sample and calibration gas control system, said control system being operably connected to the sampling line.

10. The method as recited in claim 1, in which the extraction and analysis of the emissions sample from the particular vehicle is accomplished by a remote sensing device.

11. The method as recited in claim 1, in which the extraction and analysis of the emissions sample from the particular vehicle is accomplished by on-board analyzers plumbed directly into the exhaust system of the particular vehicle.

12. A method for determining a mass of a pollutant in an emissions sample obtained from a particular vehicle, comprising the steps of:
   measuring a velocity and an acceleration rate of the particular vehicle over a testing period comprised of one or more discrete time intervals;
   measuring a concentration of the pollutant in the emissions sample at each discrete time interval;
   calculating a total drive wheel power demand at each discrete time interval based on the velocity, the acceleration rate and certain physical characteristics of the particular vehicle:
   determining an engine load and an engine speed based on the total drive wheel power demand;
   determining instantaneous fuel consumption of the particular vehicle;
   calculating an exhaust flow rate based on the instantaneous fuel consumption of the particular vehicle at each discrete time interval; and
   converting measured pollutant concentration into pollutant mass at each discrete time interval by multiplying the exhaust flow rate by the measured concentration of the pollutant by a known density of the pollutant.

13. The method as recited in claim 12, and further comprising the steps of:
   plotting the mass of the pollutant over the testing period to generate an emission profile; and
   integrating the emission profile over the testing period to determine a total mass of the pollutant.

14. The method as recited in claim 13, and further comprising the steps of:
   dividing the total mass of the pollutant by the distance traveled over the testing period to calculate a test score for the pollutant; and
   comparing said test score against a defined standard, wherein a test score exceeding the defined standard is considered a failure.

15. The method as recited in claim 12 in which the calculation of the exhaust flow rate based on the instantaneous fuel consumption of the particular vehicle is premised on an assumed combustion of fuel with a stoichiometric air-fuel ratio.

16. The method as recited in claim 12, in which measuring the concentration of the pollutant in the emissions sample is accomplished by:
   a narrow sample probe for insertion into the tailpipe of the particular vehicle;
   a sampling line operably connected to said sample probe; and
   an analyzer for detection of the pollutant associated with and in gaseous communication with a sample and calibration gas control system, said control system being operably connected to the sampling line.

17. The method as recited in claim 12, in which measuring the concentration of the pollutant in the emissions sample is accomplished by a remote sensing device.

18. The method as recited in claim 12, in which measuring the concentration of the pollutant in the emissions sample is accomplished by: on-board analyzers plumbed directly into the exhaust system of the particular vehicle.

* * * * *